United States Patent [19]

Morita

[11] Patent Number: 4,496,683
[45] Date of Patent: Jan. 29, 1985

[54] RUBBER COMPOSITIONS CONTAINING A VULCANIZATION SYSTEM ALTERATIVE

[75] Inventor: Eiichi Morita, Mililani Town, Hi.

[73] Assignee: Monsanto Company, St. Louis, Mo.

[21] Appl. No.: 407,028

[22] Filed: Aug. 11, 1982

[51] Int. Cl.³ ............................................. C08K 3/04
[52] U.S. Cl. ................................ 524/571; 524/574; 524/575; 524/575.5; 525/343; 525/332.6; 525/332.7
[58] Field of Search ............... 525/332.6, 332.7, 343; 524/571, 574, 575, 575.5

[56] References Cited

U.S. PATENT DOCUMENTS

| | | | |
|---|---|---|---|
| 1,949,629 | 3/1934 | Romieux et al. | 18/53 |
| 2,063,629 | 12/1936 | Salzberg et al. | 260/99.20 |
| 3,035,082 | 5/1962 | Lorenz | 260/461 |
| 3,109,770 | 11/1963 | Price et al. | 167/22 |
| 3,544,531 | 12/1970 | Morita | 260/79.5 |
| 3,705,923 | 12/1972 | Sullivan | 260/608 |
| 3,859,297 | 1/1975 | Sullivan | 260/306.5 |
| 3,869,435 | 3/1975 | Trivette, Jr. | 260/79.5 |
| 4,119,780 | 10/1978 | Sullivan | 548/329 |

OTHER PUBLICATIONS

Pimblott et al., "Bis(Diisopropyl)Thiophosphoryl Disulfide in Cis-1,4-Polyisoprene Vulcanization Reaction I, as a Sulfur Donor, " JACS 19, 865-877 (1975).

Primary Examiner—Joseph L. Schofer
Assistant Examiner—Bernard Lipman
Attorney, Agent, or Firm—Gordon B. Seward

[57] ABSTRACT

Compositions of vulcanizeable diene rubber, a cross-linking agent, a vulcanization accelerator and a vulcanization system alterative are disclosed, which have improved properties of scorch delay, cure rate and reversion resistance. The alterative is a compound of the formula

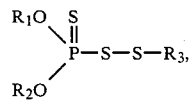

where $R_1$ and $R_2$ are the same or different radicals selected from alkyl of 1-12 carbon atoms, phenyl, cycloalkyl of 3-8 carbon atoms and alkyaryl and aralkyl of 7-12 carbon atoms, and $R_3$ is selected from the same as $R_1$ and $R_2$, optionally substituted with one or more halogen, nitro, alkoxy, carboalkoxy, acyl, acyloxy, amido, cyano, thio or sulfonyl substituents.

12 Claims, 2 Drawing Figures

RUBBER COMPOSITIONS CONTAINING A VULCANIZATION SYSTEM ALTERATIVE

BACKGROUND OF THE INVENTION

This invention relates to compounds of vulcanizable diene rubber which exhibit improved properties of vulcanization. More specifically, it relates to compositions containing vulcanizable diene rubber, which compositions, upon being heated to vulcanization temperatures for appropriate times, show improvements in scorch-delay, cure rate or reversion resistance. Still more specifically the invention relates to vulcanizable rubber which contains a vulcanizing agent such as sulfur, an accelerator of vulcanization, and an alternative which produces vulcanization behavior which is improved in at least one of several aspects.

The compounds referred to above are generally known in the art, and are identified in U.S. Pat. Nos. 3,035,082 and 3,109,770 as useful insecticides or oil additives. The general formula of these compounds is:

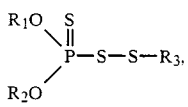

with $R_1$, $R_2$ and $R_3$ defined, in the patents, as a range of hydrocarbon radicals.

U.S. Pat. Nos. 3,705,923; 3,859,297; and 4,119,780 to A. B. Sullivan disclose and claim a method for making the compounds as described and generally teach their use as vulcanization accelerators, vulcanization agents, chemical intermediates, high pressure lubricants, fungicides, insecticides nematocides and bactericides. No suggestion in the Sullivan patents is found that the compounds should be used in combination with other accelerators. Phosphorotrithioyl-2-azoles are said to be "potent accelerators and vulcanizing agents for the vulcanization of rubber". Furthermore, the use of these compounds is outside the scope of the present invention.

BRIEF DESCRIPTION OF THE INVENTION

It has now been surprisingly found that the combination of conventional vulcanization accelerators and cross-linking agents in vulcanizable diene rubber with a vulcanization system alternative of the formula

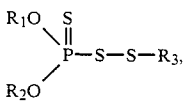

wherein $R_1$ and $R_2$ are the same or different radicals selected from alkyl of 1–12 carbon atoms, cycloalkyl of 3–8 carbon atoms and alkaryl and aralkyl of 7–12 carbon atoms, and $R_3$ is the same as $R_1$ or $R_2$, optionally substituted with one or more halogen, nitro, alkoxy, carboalkoxy, acyl, acyloxy, amido, cyano, thio or sulfonyl substituents, produces unexpected improvements in the vulcanization behavior of the rubber.

Specifically, the invention provides rubber compounds, each with at least one of the following improvements; increased scorch delay, faster cure rate and improved reversion resistance. In most instances, more than one of these improvements is realized, and often all three improvements are achieved. When slower accelerators, such as MBT or MBTS are used, the alterative also increases the state of cure as evidenced by increased cross-link density and modulus.

Scorch delay is the time before appreciable pre-cure or scorch occurs in a rubber compound when it is heated to vulcanizing temperatures. An increase in scorch delay provides a safety margin in processing, handling and shaping the rubber before it is vulcanized. The value of a faster cure (or vulcanization) rate is easily recognized as permitting faster production rates. Improved reversion resistance is also a valuable property, minimizing the degradation in properties that can occur on overcure of a rubber compound. Where thick sections are cured, as in an off-the-road tire tread, the problem can be serious.

An improvement in any one of the important properties mentioned can be of value in producing tires or other rubber products, however, a simultaneous improvement in two or more of these properties is a fortunate and unexpected result. When, as often happens, all three properties are improved, rubber articles can be manufactured with greater processing safety tolerances, faster throughput, and little danger of damage due to overcure or non-oxidative aging.

DETAILED DESCRIPTION OF THE INVENTION

Figure 1:
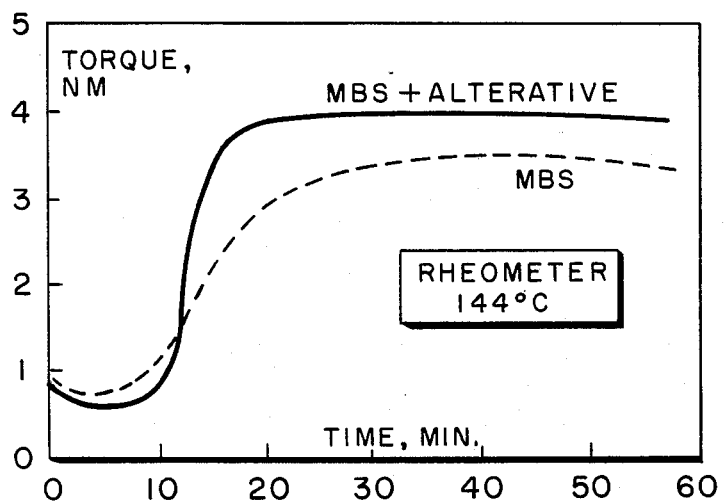
FIGS. 1 and 2 are Rheographs generated by a Rheometer measuring the resistance to deformation of a rubber compound with time while the compound is being cured.

A vulcanizable diene rubber is a polymer from a diene monomer. It is either a natural or synthetic polymer, or a mixture of two or more natural and synthetic polymers. Natural diene rubber includes Hevea rubber, in the form of smoked sheet, crepe or other typical forms, guayule, and other naturally occurring elastomers. Synthetic polymers which are included in the definition of "diene rubber" include polymers from isoprene and butadiene, either homopolymers or copolymers with one or more co-monomers which can be dienes or other copolymerizable materials. For example, copolymers of isoprene or butadiene with styrene, acrylonitrile, isobutylene, or unsaturated carboxy acids and esters such as maleic, fumaric, itaconic, acrylic and methacrylic acids and methylmethacrylate are included. EPDM rubbers (polymers from ethylene, propylene and a non-conjugated diene monomer) are also included. Preferred are natural rubber, polybutadiene, synthetic polyisoprene and copolymers of styrene and butadiene (SBR).

Cross-linking agents include sulfur and certain organic compounds containing sulfur which are capable of cross-linking vulcanizable diene rubber. The organic cross-linking agents include dimorpholinodisulfide and alkyl phenol disulfides. The preferred cross-linking agent is sulfur.

The mercaptoazole accelerators include compounds of the formula

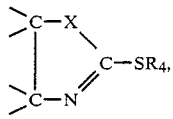

wherein the unsatisfied valences on the vicinal carbon atoms are attached to hydrogen, lower alkyl, benzyl, acetyl, carboalkoxy or phenyl or together with the carbon atoms form an aliphatic or ortho arylene ring, or two of the unsatisfied valences are joined to form a double bond. The ortho arylene ring may be substituted by lower alkyl, halo, nitro, hydroxy, carboalkoxy, acetyl, lower alkoxy and phenyl radicals, and X is S, O or NH. Lower alkyl means radicals containing 1–5 carbon atoms. $R_4$ is hydrogen or a thiyl radical having the general formula

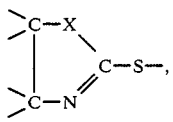

wherein the dangling valences of the carbon atoms are treated as above.

Specific examples of azole accelerators are 2-mercaptothiazole, 2-mercaptothiazoline, 2-mercaptoxazole, 2-mercaptoxazoline, 2-mercaptoimidazole, 2-mercaptobenzothiazole, 2-mercaptobenzoxazole, 2-mercaptobenzimidazole, 2-mercaptonaphthathiazole, 2-mercapto-4-methylthiazole, 2-mercapto(dihydrobenzothiazole), 2-mercapto-(4, 5, 6, 7-tetrahydrobenzothiazole), 2-mercapto-(4-n-butyloxazole), 2-mercapto-(4, 5-dimethylimidazole), 2-mercapto-(4, 5-di-n-butyloxazole), 2-mercapto-(4, phenyl-5 methylthiazole), 2-mercapto-(5-acetyl-4-methylthiazole), 2-mercapto-(5-carbethoxy-4-methylthiazole), 2-mercapto-(5-chlorobenzoxazole), 2-mercapto-(6-ethoxybenzimidazole), 2-mercapto-(5-carbethoxybenzothiazole), 2-mercapto-(6-nitrobenzimidazole), 2-mercapto-(5, 6-diethylbenzoxazole), 2-mercapto (4-methylthiazoline), 2-mercapto-(4-methoxythiazoline), and 2,2'-dithiobisbenzothiazole. Of the azoles, thiazole is preferred; of the mercaptoazole accelerators most preferred are 2-mercaptobenzothiazole and 2,2'-dithiobisbenzothiazole (also known as benzothiazyl disulfide, or MBTS).

Sulfenamide accelerators include azole sulfenamides, based on the mercaptoazoles disclosed above. They have the general formula

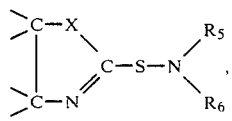

wherein the azole portion of the formula is as defined above for the mercaptoazoles, and $R_5$ and $R_6$ are the same or different, selected from hydrogen, lower alkyl, cycloalkyl of 3–8 carbon atoms, phenyl, substituted phenyl, and $R_5$ and $R_6$ along with the nitrogen atom can form a heterocycle of 4–8 carbon atoms with or without an oxygen atom. Preferred are the thiazole sulfenamides, and most preferred are the benzothiazolesulfenamides.

Specific examples of sulfenamide accelerators used in the composition of the invention include N-cyclohexyl-2-benzothiazyl sulfenamide, N-t-butyl-2-benzothiazylsulfenamide, N,N-dicyclohexyl-2-benzothiazylsulfenamide, N,N-diethyl-2-benzothiazylsulfenamide, N,N-diisopropyl-2-benzothiazylsulfenamide, N-oxydiethylene-2-benzothiazylsulfenamide and N-isopropyl-2-benzothiazylsulfenamide. All of the compounds enumerated above are preferred species of sulfenamide accelerators.

Thiourea accelerators which are useful in the composition of the invention include thiourea and hydrocarbon-substituted thioureas such as N,N'-dibutylthiourea, trimethylthiourea, N,N'-diethylthiourea, tetramethylthiourea and ethylenethiourea.

Thiuram accelerators include thiuram mono-, di- and polysulfides of the general formula;

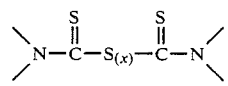

wherein x is an integer of from 1 to 10 and the unsatisfied valences of the N atoms are attached to hydrogen, lower alkyl, cycloalkyl, phenyl and substituted phenyl substituents.

Preferred thiuram accelerators include N, N'-dimethyl-N,N'-diphenyl thiuram disulfide, dipentamethylene thiuram hexasulfide, tetrabutylthiuram monosulfide, tetraethylthiuram disulfide, tetramethylthiuram disulfide, tetramethylthiuram monosulfide and dimethyl morpholino thiuram disulfide.

Xanthate accelerators useful in the compositions of the invention contain the radical:

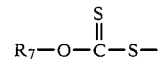

wherein $R_7$ is alkyl, cycloalkyl, phenyl, and alkyl-substituted phenyl of 1–20 carbom atoms. Specific examples include dibutylxanthogen disulfide and zinc dibutyl xanthate.

dithiocarbamate accelerators used in the compositions are characterized by the general formula:

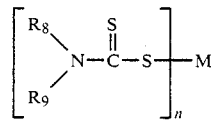

wherein n is an integer of 1–8, M is a metal or a quaternary ammonium ion, and $R_8$ and $R_9$ are the same or different, selected from 1–20 carbon alkyl, alkaryl, aralkyl, cycloalkyl, phenyl, substituted phenyl, and $R_8$ and $R_9$ along with the nitrogen atom can form a heterocycle of 4–8 carbon atoms, with or without an added oxygen atom.

Examples of $R_8$ and $R_9$ are methyl, ethyl, propyl, isopropyl, n-butyl, isobutyl, sec-butyl, tert-butyl, n-amyl, hexyl, octyl, decyl, eicosyl, cyclopentyl, cyclohexyl, phenyl, benzyl, phenethyl and tolyl. Specific examples of M are zinc, lead, iron (ferric), copper, cadmium, selenium, tellurium, sodium, potassium, bismuth, dimethylammonium, dimethylcyclohexylammonium, cyclohexylethylammonium and piperidinium. Preferred dithiocarbamate accelerators include zinc dibutyldithiocarbamate, zinc diethyldithiocarbamate, zinc dimethyldithiocarbamate and dimethylcyclohexylammonium dibutyldithiocarbamate.

Guanidine acclerators useful in the method of the invention are those having the general formula

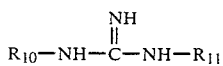

wherein $R_{10}$ and $R_{11}$ can be alkyl of 1–20 carbon atoms, cycloalkyl of 3–10 carbon atoms, aryl, aralkyl or alkaryl, or

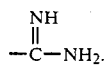

Preferred are diphenylguanidine, di-ortho-tolylguanidine, and ortho-tolylbiguanide.

In the composition of the invention, in addition to vulcanizable diene rubber a cross-linking agent and an accelerator, a vulcanization system alterative of the formula:

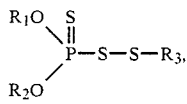

is also present, wherein $R_1$ and $R_2$ are the same or different selected from alkyl of 1 to 12 carbon atoms, phenyl, cycloalkyl of 3–8 carbon atoms, and alkaryl or aralkyl of 7–12 carbon atoms, and $R_3$ is selected from the same as $R_1$ or $R_2$, optionally substituted with one or more halogen, nitro, alkoxy, carbalkoxy, acyl, acyloxy, amido, cyano, thio or sulfonyl sybstituents.

Examples of $R_1$ and $R_2$ are methyl, ethyl, n-propyl, isopropyl, n-butyl, sec-butyl, isobutyl, tert-butyl, n-amyl, isoamyl, sec-amyl, n-hexyl, n-octyl, n-decyl, n-dodecyl, cyclopropyl, cyclobutyl, cyclopentyl, cyclohexyl, cycloheptyl, cyclooctyl, phenyl, benzyl, totlyl and phenethyl. Preferred are phenyl and 3–8 carbon alkyl.

Examples of $R_3$ include all of the radicals exemplary of $R_1$ and $R_2$ above, and 2-chloroethyl, 3-nitro-n-amyl, 3-methoxy-n-hexyl, 2-carbomethoxyethyl, p-chlorophenyl, m-nitrophenyl, o-carbomethoxyphenyl 2-acetoxyethyl, 2-(isobutyraldehydo), N,N-dimethylamidomethyl, 2-cyanoethyl, 2-(methylthio)-ethyl, methyl lactyl and 2-(methylsulfonyl) ethyl. Preferred are 2–8 carbon alkyl, benzyl, cyclohexyl and phenyl, optionally substituted by a chloro or carboalkoxy group.

Usually $R_1$ and $R_2$ are the same, and $R_3$ differs from them. Other compounds effective as alteratives in the invention are disclosed in Lorenz U.S. Pat. No. 3,035,082, the disclosure of which patent is incorporated herein by reference.

The cross-linking agent is preferably used in amounts of from 0.2 to 4 parts by weight per 100 parts by weight of rubber, as desired. Sulfur is the preferred cross-linking agent; however, both sulfur and an organic sulfur-containing cross-linking agent can be used. In any case, the amount and type of cross-linking agent used will be dictated primarily by the properties desired in the vulcanized rubber.

The amount of the vulcanization accelerator used in the composition of the invention is preferably from 0.1 to 5.0 parts by weight per 100 parts of the rubber by weight. More preferably, from 0.2 to 2.0 parts of accelerator is used.

The alterative compound is used in an amount of from 0.1 to 5.0 parts by weight. A preferable range is from 0.2 to 2.0 parts by weight. Two or more different alternatives can be used; however, little advantage is usually realized in using more than one.

In addition to the cross-linking agent, accelerator and the alterative, the rubber can contain other compounding ingredients, including carbon black, other fillers, oil, zinc oxide, stearic acid and antidegradants. These materials are mixed into the rubber by using a mill or a Banbury mixer.

In order to evaluate the effect of various combinations of cross-linking agents, accelerators and alteratives in rubber, a number of standard tests are performed both on uncured and cured samples. Rubber compounds based on the compositions of the invention, together with suitable control compounds, are compared for Mooney Scorch, oscillating disc Rheometer values, stress-strain (cured samples) and other test data.

In the Mooney Scorch evaluation uncured samples are tested for processing safety or scorch delay at 135° C. The various stocks are heated to 135° C. in a Mooney Plastometer. The time, in minutes, required for the viscosity of the stock to increase 5 units above the minimum viscosity is determined. These values are commonly known as "Mooney Scorch Time" ($t_5$). The additional time required to reach 35 units above the minimum reading ($t_{35}$) offers some inverse measure of the speed of cure.

Rheometer results are obtained with the Monsanto Oscillating Disc Rheometer, described by Decker, Wise and Guerry in *Rubber World,* December 1962, page 68. The times to reach two rheometer units above the minimum viscosity ($t_2$) and the times to reach 90% of the maximum torque ($t_{90}$) are measured. The value ($t_{90} - t_2$) gives another inverse indication of the speed of the cure. Rmax, the maximum torque (in Nm), is also recorded. Rheometer values are determined at 144° C. and/or 153° C. Rheometer curves, plotting torque against elapsed time, are also generated, affording a graphic analysis of the vulcanization behavior of a sample.

Stress-strain properties of cured specimens of the compositions are measured in the conventional manner by using the procedures outlined in ASTM D-412. Tensile and modulus data are expressed in megapascals (MPa).

The alteratives of the invention can be prepared in any of several ways. In U.S. Pat. No. 3,035,082, similar compounds are prepared by reacting salts of thiosulfonic monoesters with thionothiolphosphoric acid diesters, thiono-thiolphosphonic acid monoesters, their corresponding S- or N-analogues or thiono-thiol-phosphinic acids.

U.S. Pat. No. 3,109,770 shows preparation of compounds of the formula:

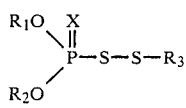

by the reaction of

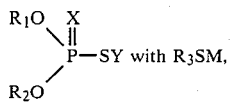

or by the reaction of

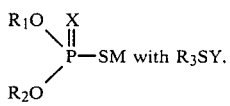

where X is oxygen or sulfur, Y is halogen and M is alkali metal.

U.S. Pat. No. 4,119,780 teaches the preparation of compounds by the reaction, for example, of a thioimide with a phosphorodithioic acid.

A preferred method of preparing the compounds is according to the reactions:

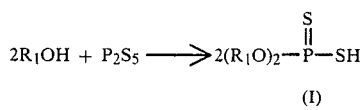

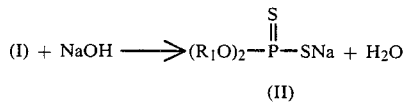

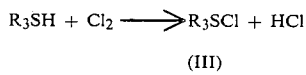

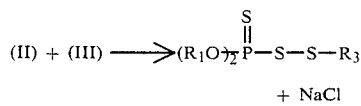

The above procedure is effective if $R_1$ and $R_2$ are the same.

EXAMPLE I

The following procedure is followed for the preparation of β-(di-n-butylphosphorodithioylthio)propionic acid, methyl ester, having the following structural formula:

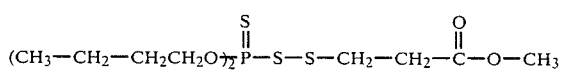

Into a three-neck, round-bottom flask equipped with a distilling head, thermometer, mechanical stirrer and an outlet to two NaOH traps are charged 61 g butanol. The flask and contents are heated to 60° C. under positive $N_2$ pressure, then 44 g $P_2S_5$ are added to form a heel. The temperature rises to about 73° C., and is maintained at 73°–75° C. under agitation for 30 minutes. The remainder (178,2 g) of the $P_2S_5$ is then added, all at once, and butanol is charged dropwise so that the temperature stays at 75°–85° C. No external application of heat is required. After all the butanol (a total of 304.9 g) is added, agitation is continued for 90 minutes, with heating as required to keep the contents above 65° C. The contents are then cooled for 15 minutes and $N_2$ is bubbled through the liquid contents to remove $H_2S$. The contents are then filtered and stripped, removing less than 1 g $P_2S_5$. Stripping is accomplished at 45° under a partial vacuum. The yield is 469.3 g, calculated as 96.8% of the product,

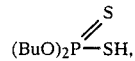

dibutyl dithiophosphoric acid, which is dissolved in heptane and cooled to room temperature.

To one mole (242.2 g) of the cooled product in heptane is added 38.8 g (0.97 mole) of NaOH in solution in 250 ml of water at room temperature, while cooling with an ice bath, controlling the temperature to 45° C. or lower. The mixture is further stirred for 30 minutes while its temperature drops to between 25° and 30° C. Two layers separate. The upper (organic) layer is very light green; the (aqueous) lower layer is a pale green-yellow, and has a pH of ~11. The sodium salt of the dithiophosphoric acid is contained in the aqueous layer.

Separately,

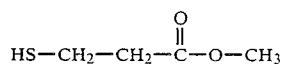

is chlorinated by reaction with an equimolar amount of chlorine in chlorobenzene at 0°–5° C. The reaction is followed with a thermometer and the off-gases are trapped in water and monitored with a conductivity meter. Approximately 0.45 g/min of chlorine is fed over a period of about 150 minutes. An endpoint is signaled by a slight temperature rise. The product sulfenyl chloride compound is purged of HCl with a nitrogen flow.

In the final step the sodium phosphorodithioate and sulfenyl chloride compound are reacted to produce the desired alterative. To 256.4 g (0.97 mole) of sodium dibutyl phosphorodithioate in water solution is added, dropwise, 150 g (0.97 mole) of 2-carbomethoxychloro-sulfenylethane in chlorobenzene solution with agitation over the period of an hour at room temperature. After agitation of 15 minutes more, the phases are allowed to separate, and the pH of each is measured. Both phases have an initial pH of 5, which, in the chlorobenzene layer, slowly declines to 2. In order to facilitate separation, the organic layer is extracted twice, using 250 ml of 2% HCl each time.

The organic layer is then extracted twice with 250 ml of 2% NaOH, then with 150 ml, then 100 ml saturated NaCl solution. 290 g of greenish liquid is recovered, which is assayed, by HPLC analysis, after stripping, at 80% of the desired product, the remainder being principally the disulfides of the phosphorodithioic acid and of the sulfenyl chloride. The elemental analysis of the desired product gave 8.6% phosphorus and 26.7% sulfur, against 8.74 and 26.39%, respectively, calculated.

EXAMPLE II

O,O'-Di-n-butyl-S-benzylthiophosphorodithioate is produced, using a different procedure from that of Example I. Benzylthiosuccinimide is first prepared by reacting N-chlorosuccinimide with benzyl mercaptan with triethylamine as an acid acceptor. 5.5 g of the benzylthiosuccinimide is then combined with dibutyldithiophlsphoric acid (6.05 g) and 100 ml toluene in a 250 ml erlenmeyer flask. The contents of the flask are stirred and heated to 60° C. for four hours. The heat source is then removed and the flask and its contents are allowed to cool to room temperature, with continuing agitation. With HPLC liquid chromatograph analysis having indicated the absence of starting materials, the product is filtered to remove succinimide and the filtrate is washed twice with 50 ml of water each time and four times with 60 ml of 10% $Na_2CO_3$ in each case. Elemental analysis gives 8.76% P, 26.51% S, compared with 8.50% and 26.39% calculated, respectively.

In a similar manner, other variations of the above compound are prepared, in which $R_3$ of the general formula:

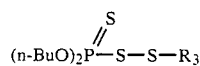

is phenyl, t-butyl, n-octyl, p-chlorophenyl, o-carboxymethylphenyl, m-nitrophenyl and cyclohexyl.

EXAMPLE III

In order to evaluate the effect of the combination of the alterative and known accelerators on the behavior of a rubber compound, a series of compounds is prepared, based on he following natural rubber masterbatch:

| Material | Parts |
|---|---|
| Natural Rubber - SMR 5CV | 100 |
| Carbon Black - N-330 | 50 |
| Processing Oil - Sundex 790 | 3.0 |
| Zinc Oxide | 5.0 |
| Stearic Acid | 2.0 |
| Antidegradant* | 2.0 |
| Total | 162.0 |

*N—1.3-dimethylbutyl-N'—phenyl-p-phenylenediamine

Rubber compounds are prepared containing, in addition to the masterbatch, 2.5 parts of sulfur and 0.5 parts of an accelerator, by using each of the following commercial accelerators:

| Accelerator | Code |
|---|---|
| N—t-Butyl-2-benzothiazylsulfenamide | TBBS |
| N—Cyclohexyl-2-benzothiazylsulfenamide | CBS |
| 2-Morpholino-benzothiazylsulfenamide | MBS |
| N,N—Diisopropyl-2-benzothiazylsulfenamide | DIBS |
| N,N—Dicyclohexyl-2-benzothiazylsulfenamide | DCBS |
| 2,2'-Dithiobisbenzothiazole | MBTS* |
| 2-Mercaptobenzothiazole | MBT |
| N,N'—Dimorpholinodithiocarbamate | OTOS |
| Tetramethylthiuram disulfide | TMTD |
| 2-(Morpholinodithio)-benzothiazole | BDTM |
| Zinc dibutyldithiocarbamate | ZBDC |

*this accelerator is run both at 0.5 parts and 1.0 parts.

The compounds are mixed and tested for Mooney scorch at 135° C., Rheometer values, both at 144° C. and at 160° C. are obtained, and cured samples are stress-strain tested. The data and results are set forth in Tables I and II.

The data show that the most preferred alterative, in combination with any of the eleven different accelerators tested, produces improvements in scorch delay, cure rate or reversion resistance, and in most instances in all three of these properties.

The amount of scorch delay can be interpreted from the data on Mooney scorch $t_5$ and from the Rheometer $t_2$ values. It is evident that, with the exception of some of the data points for the delayed-action accelerators TBBS, and CBS, longer scorch times are achieved by adding 1.0 part of the alterative. In all instances, cure times are reduced, as best seen in the Rheometer data $(t_{90}-t_2)$. The degree of reversion can be expressed in a variety of ways, for example, as $\Delta t_{-5}$, the time required for a 5-unit drop from maximum torque; as $t_{-90}$ the time to revert to 90% of the maximum torque; as $\Delta t_{-95}$, the time to revert from maximum torque to 95% of maximum torque; and as % $\Delta R_{60}$, the percent torque decay from maximum after 60 minutes at 160° C. (All of these values are merely interpretations, in different ways, of the loss of Rheometer torque after the sample is fully cured). In all instances, the addition of 1.0 part of the alterative improved the reversion resistance substantially. Hardness is in Shore A units.

TABLE I

| | | Primary Accelerator Type | | | | | | | | | | |
|---|---|---|---|---|---|---|---|---|---|---|---|---|
| | | TBBS | | CBS | | MBS | | DIBS | | DCBS | | MBTS |
| Masterbatch | | 162.0 | → | → | → | → | → | → | → | → | → | → |
| Sulfur | | 2.5 | → | → | → | → | → | → | → | → | → | → |
| Primary Accelerator | | 0.5 | → | → | → | → | → | → | → | → | 1.0 | → |
| Alterative | | — | 1.0 | — | 1.0 | — | 1.0 | — | 1.0 | — | 1.0 | — | 1.0 |
| Mooney | $t_5$, min. | 12.0 | 11.6 | 11.0 | 11.1 | 9.5 | 14.8 | 10.5 | 11.5 | 10.5 | 17.5 | 5.5 | 7.0 |
| Scorch at | $t_{35}$, min. | 14.0 | 12.9 | 12.6 | 12.1 | 12.4 | 15.7 | 14.5 | 17.1 | 16.0 | 19.1 | 7.0 | 9.4 |
| 135° C. | Min. Visc. | 32.5 | 33.9 | 40.5 | 37.5 | 45.5 | 37.0 | 43.0 | 39.0 | 40.0 | 33.1 | 38.1 | 40.9 |
| Rheometer | $t_2$, min. | 8.3 | 7.8 | 8.3 | 7.7 | 8.3 | 9.7 | 9.2 | 11.0 | 9.0 | 11.2 | 4.2 | 5.0 |
| at 144° C. | $t_{90}$, min | 21.5 | 13.0 | 21.3 | 13.2 | 23.8 | 16.0 | 32.0 | 17.0 | 34.5 | 17.7 | 16.8 | 12.3 |
| | $t_{90}-t_2$, min. | 13.2 | 5.2 | 13.0 | 5.5 | 15.5 | 6.3 | 22.8 | 6.0 | 25.5 | 6.5 | 12.7 | 7.3 |
| | Rmax (Nm) | 4.15 | 4.62 | 3.96 | 4.44 | 3.89 | 4.45 | 3.83 | 4.45 | 3.66 | 4.36 | 3.57 | 4.52 |
| Rheometer | $t_2$, min. | 3.2 | 3.8 | 3.2 | 3.3 | 3.0 | 4.2 | 3.3 | 4.7 | 3.7 | 3.7 | 2.2 | 2.5 |
| at 160° | $t_{90}$, min. | 7.8 | 5.5 | 7.5 | 5.2 | 8.3 | 6.2 | 10.8 | 6.8 | 12.2 | 7.0 | 6.5 | 4.8 |
| | $t_{90}-t_2$, min. | 4.7 | 1.7 | 4.3 | 1.8 | 5.3 | 2.0 | 7.5 | 2.2 | 8.5 | 2.3 | 4.3 | 2.3 |
| Reversion | $\Delta t_{-5}$, min. | 8.5 | 47 | 9 | 45 | 10 | 55 | 10 | 46 | 12 | 24 | 14 | 90 |
| Time. | $\Delta t_{-90}$, min. | 9.5 | 72 | 9 | 87 | 9.5 | 70 | 9 | 85 | 11 | 42 | 9 | 110 |
| Stress-Strain | Cure Time, min | 25 | 14 | 25 | 14 | 28 | 18 | 35 | 18 | 38 | 18 | 20 | 16 |
| t$_{95}$ Cure | Hardness | 64 | 65 | 63 | 64 | 61 | 67 | 60 | 66 | 59 | 63 | 60 | 66 |
| (144° C.) | $M_{100}$ (MPa) | 2.73 | 3.35 | 2.54 | 3.28 | 2.62 | 3.30 | 2.47 | 3.25 | 2.31 | 3.05 | 2.28 | 3.26 |
| | $M_{300}$ (MPa) | 13.58 | 15.20 | 12.93 | 14.85 | 12.82 | 15.02 | 11.95 | 14.77 | 11.43 | 14.45 | 10.77 | 14.69 |
| | UTS (MPa) | 30.3 | 30.0 | 29.2 | 28.8 | 29.2 | 29.9 | 29.0 | 28.0 | 28.1 | 30.0 | 28.4 | 26.3 |

TABLE I-continued

| | Primary Accelerator Type | | | | | | | | | | | |
|---|---|---|---|---|---|---|---|---|---|---|---|---|
| | TBBS | | CBS | | MBS | | DIBS | | DCBS | | MBTS | |
| UE, % | 574 | 553 | 569 | 524 | 569 | 544 | 594 | 513 | 587 | 548 | 608 | 478 |

TABLE II

| | | Primary Accelerator Type | | | | | | | | | | | |
|---|---|---|---|---|---|---|---|---|---|---|---|---|---|
| | | MBTS | | MBT | | OTOS | | TMTD | | BDTM | | ZBDC | |
| Masterbatch | | 162.0 | → | → | → | → | → | → | → | → | → | → | → |
| Sulfur | | 2.5 | → | → | → | → | → | → | → | → | → | → | → |
| Primary Accelerator | | 0.5 | → | → | → | → | → | → | → | → | → | → | → |
| Alterative | | — | 1.0 | — | 1.0 | — | 1.0 | — | 1.0 | — | 1.0 | — | 1.0 |
| Mooney | $t_5$, min. | 6.5 | 8.1 | 5.4 | 7.5 | 6.7 | 11.0 | 4.4 | 6.7 | 10.5 | 8.9 | 4.0 | 9.0 |
| Scorch | $t_{35}$, min. | 8.1 | 10.0 | 6.5 | 8.6 | 8.9 | 12.6 | 5.0 | 7.1 | 12.7 | 9.9 | 4.7 | 10.9 |
| at 135° C. | Min. Visc. | 51.1 | 49.9 | 58.5 | 51.0 | 55.9 | 50.1 | 57.1 | 51.0 | 52.9 | 49.5 | 56.0 | 50.0 |
| Rheometer | $t_2$, min. | 5.3 | 6.3 | 4.7 | 5.3 | 5.8 | 3.0 | 3.0 | 4.7 | 8.3 | 6.3 | 3.0 | 7.0 |
| at 144° C. | $t_{90}$, min. | 25.5 | 12.0 | 25.5 | 10.5 | 16.0 | 9.3 | 6.0 | 7.7 | 22.5 | 10.7 | 9.3 | 11.5 |
| | $t_{90} - t_2$, min. | 20.2 | 5.7 | 20.8 | 5.2 | 10.2 | 6.3 | 3.0 | 3.0 | 14.2 | 4.3 | 6.3 | 4.5 |
| | $R_{max}$ (Nm) | 2.88 | 4.14 | 2.89 | 4.07 | 3.49 | 2.96 | 3.92 | 4.09 | 3.26 | 4.14 | 2.96 | 3.59 |
| Rheometer | $t_2$, min. | 2.3 | 2.8 | 2.2 | 2.5 | 2.7 | 3.3 | 1.7 | 2.3 | 3.3 | 2.7 | 1.7 | 3.2 |
| at 160° C. | $t_{90}$, min. | 8.8 | 4.8 | 9.5 | 4.3 | 7.3 | 5.7 | 3.2 | 3.7 | 8.3 | 4.5 | 4.5 | 5.2 |
| | $t_{90} - t_2$, min. | 6.5 | 2.0 | 7.3 | 1.8 | 4.7 | 2.3 | 1.5 | 1.3 | 5.0 | 1.8 | 2.8 | 2.0 |
| Reversion | $\Delta t_{-95}$, min. | 9 | 31 | 11 | 47.5 | 4.5 | 3.5 | 1.7 | 3.3 | 9.5 | 6.0 | 2.5 | 3.5 |
| Time | % $\Delta R_{60}$ | 13.9 | 4.4 | 11.6 | 4.0 | 18.7 | 12.2 | 17.3 | 7.7 | 17.0 | 9.2 | 12.9 | 5.6 |
| Stress-Strain | Cure Time, min. | 30 | 12 | 30 | 12 | 19 | 15 | 7 | 7 | 30 | 12 | 12 | 12 |
| $t_{95}$ Cure | Hardness | 59 | 65 | 58 | 65 | 62 | 67 | 65 | 67 | 60 | 65 | 60 | 63 |
| (144° C.) | $M_{100}$ (MPa) | 1.77 | 2.93 | 1.75 | 2.79 | 2.36 | 2.85 | 3.08 | 2.93 | 2.23 | 2.88 | 2.05 | 2.20 |
| | $M_{300}$ (MPa) | 8.55 | 13.95 | 8.53 | 13.75 | 11.69 | 13.87 | 14.29 | 13.93 | 11.14 | 13.51 | 10.47 | 10.77 |
| | UTS (MPa) | 18.8 | 26.7 | 20.7 | 23.7 | 27.6 | 26.9 | 28.6 | 25.5 | 24.3 | 25.9 | 25.9 | 22.6 |
| | UE, % | 531 | 495 | 552 | 456 | 569 | 503 | 529 | 476 | 528 | 493 | 576 | 527 |

In the drawings, FIG. 1 is a Rheograph, depicting 144° C. cure curves for the fifth and sixth compounds in Table 1. The dashed line shows the torque-time relationship for the compound without the alterative, and the solid line for the compound containing the alterative. The accelerator in both compounds, 2-morpholinobenzothiazylsulfenamide (MBS) is a so-called delayed action accelerator. Thus, the scorch time is only very slightly longer for the compound containing the alterative. ($t_2$ is 9.7 min. compared to 8.3 min. for the control.) From the steepness of the curves it can be seen that the sample containing the alterative develops its maximum torque much faster than does the control. The flatness of the curve thereafter shows that the compound containing the alterative is more resistant to reversion than the control.

Figure 2:
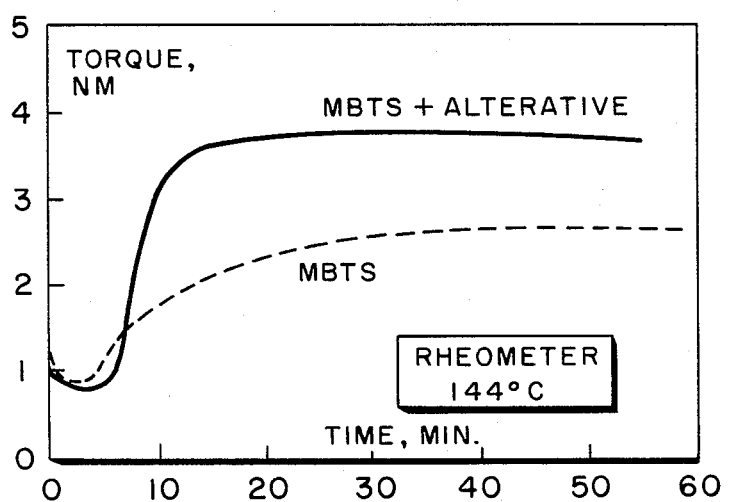

FIG. 2 depicts a similar Rheograph, this time for the first two compounds in Table II, wherein the accelerator is 2,2'-dithiobisbenzothiazole (MBTS). From these curves it can be seen that MBTS by itself is scorchy and slow curing. Since the curve stops before 60 minutes, it does not show reversion in the control compound; however, the data in Table II on reversion, derived from Rheometer data at 160° C., clearly show that, in addition to providing scorch delay and a faster cure, the alterative improves reversion resistance in a compound which has MBTS as its accelerator.

EXAMPLE IV

To evaluate the effectiveness of a number of alteratives within the definition thereof, a series of compounds are evaluated in the same masterbatch used in Example III. To this masterbatch is added, in each case, 2.5 parts of sulfur and 0.5 parts of t-butyl-2-benzothiazylsulfenamide as an accelerator per 100 parts by weight of rubber. In addition to a control compound with no other additive, nine different alteratives are compared, as well as two other additives outside the scope of the present invention, each at the level of 1.0 parts per 100 parts of rubber by weight.

The compounds are tested as in Example III. Formulations and test results are shown in Table III. The alteratives used are all of the general formula:

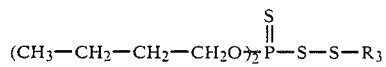

Of the three stocks which contain no alterative, one is a control with no other additive, one contains 1.0 part of the compound

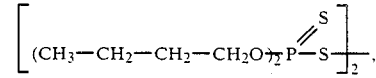

identified as "PDS", and the remaining composition contains 1.0 part of

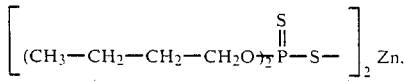

identified as "ZBDP".

TABLE III

| | | control | Methyl propionate | benzyl | o-carbo-methoxy phenyl | phenyl | t-butyl | n-octyl | p-chloro-phenyl | m-nitro phenyl | cyclo-hexyl | PDS | ZBDP |
|---|---|---|---|---|---|---|---|---|---|---|---|---|---|
| Masterbatch | | 162.0 | → | → | → | → | → | → | → | → | → | → | → |
| Sulfur | | 2.5 | → | → | → | → | → | → | → | → | → | → | → |
| TBBS | | 0.5 | → | → | → | → | → | → | → | → | → | → | → |
| Additive | | — | 1.0 | → | → | → | → | → | → | → | → | → | → |
| Mooney | $t_5$, min | 10.7 | 10.8 | 10.2 | 10.4 | 11.1 | 14.3 | 12.0 | 10.2 | 8.4 | 13.7 | 8.2 | 5.9 |
| Scorch at | $t_{35}$, min | 12.8 | 12.0 | 11.4 | 11.5 | 12.4 | 15.6 | 13.5 | 11.4 | 9.4 | 15.1 | 9.1 | 6.6 |
| 135° C. | min. vis. | 39.0 | 35.0 | 29.9 | 34.2 | 32.5 | 36.0 | 36.0 | 33.5 | 31.3 | 39.8 | 40.1 | 39.9 |
| Rheometer | $t_2$, min | 8.0 | 7.8 | 7.1 | 7.2 | 7.7 | 9.8 | 8.2 | 7.2 | 5.5 | 9.5 | 5.2 | 4.0 |
| at | $t_{90}$, min | 21.3 | 12.3 | 11.0 | 11.7 | 12.0 | 17.3 | 13.0 | 11.3 | 9.5 | 14.7 | 9.0 | 8.0 |
| 144° C. | $t_{90} - t_2$, min | 13.3 | 4.5 | 4.9 | 4.5 | 4.3 | 7.5 | 4.8 | 4.2 | 4.0 | 5.2 | 3.8 | 4.0 |
| | $R_{max}$, Nm | 3.96 | 4.28 | 4.30 | 4.19 | 4.18 | 3.99 | 4.15 | 4.22 | 4.28 | 4.21 | 4.43 | 4.28 |
| Reversion | % $\Delta R_{60}$ | 21.6 | 6.6 | 6.5 | 9.9 | 10.3 | 10.2 | 8.6 | 10.4 | 10.2 | 7.8 | 3.9 | 6.2 |
| based on | $\Delta t_{-95}$, min | 6 | 23 | 24 | 9 | 10 | 7 | 14 | 10 | 10 | 13.5 | 53 | 31 |
| Rheometer at 160° C. | | | | | | | | | | | | | |
| Stress- | Cure Time | 26 | 13 | 13 | 13 | 13 | 19 | 13 | 13 | 10 | 16 | 10 | 10 |
| Strain | hardness | 67 | 71 | 71 | 70 | 71 | 69 | 69 | 70 | 68 | 69 | 71 | 70 |
| cured at | $M_{100}$, (MPa) | 3.32 | 3.90 | 3.87 | 3.74 | 3.81 | 3.68 | 3.67 | 3.82 | 3.52 | 3.47 | 3.99 | 4.03 |
| 144° C. | $M_{300}$, (MPa) | 15.6 | 17.6 | 17.3 | 16.7 | 17.0 | 17.0 | 17.3 | 17.1 | 16.3 | 16.1 | 17.2 | 17.4 |
| | UTS (MPa) | 28.1 | 26.9 | 24.4 | 25.7 | 27.3 | 28.1 | 27.8 | 27.2 | 27.6 | 27.0 | 25.7 | 27.3 |
| | UE, % | 500 | 462 | 407 | 445 | 478 | 470 | 469 | 456 | 482 | 462 | 439 | 449 |

The data in Table III show, generally, that all of the alteratives are effective. The control with no additive is predictably slow-curing, and has relatively low reversion resistance. The compound containing PDS exhibits very good reversion resistance, but its scorch delay is substantially worse than that of the control with no additive. The stock containing ZBDP is even worse in this respect.

The compositions of the invention have been shown to possess improved properties relating to their processing, vulcanization and final properties. As a result, they are useful in the production of rubber articles of all types, including tires, belts, hose, sheeting, molded articles and the like.

Although the invention has been illustrated by typical examples, it is not limited thereto. Changes and modifications of the examples of the invention herein chosen for purposes of disclosure can be made which do not constitute departure from the spirit and scope of the invention.

The embodiments of the invention in which an exclusive property or privilege is claimed are defined as follows:

1. A composition comprising vulcanizable diene rubber, a cross-linking agent, a vulcanization accelerator selected from azoles, sulfenamides, thioureas, thiurams, xanthates, dithiocarbamates and guanidines and from 0.1 to 5.0 parts by weight per 100 parts of the rubber by weight of a vulcanization system alterative of the formula

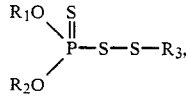

wherein $R_1$ and $R_2$ are the same or different radicals selected from alkyl of 1-12 carbon atoms, phenyl, cycloalkyl of 3-8 carbon atoms and alkaryl and aralkyl of 7-12 carbon atoms, and $R_3$ is selected from the same radicals as $R_1$ or $R_2$, optionally substituted with one or more halogen, nitro, alkoxy, carboalkoxy, acyl, acyloxy, amido, cyano, thio or sulfonyl substituents.

2. The composition of claim 1 wherein the cross-linking agent is sulfur.

3. The composition of claim 2 wherein the vulcanization accelerator is present in an amount of from 0.1 to 5.0 parts by weight per 100 parts by weight of the rubber.

4. The composition of claim 2 wherein the alterative is present in an amount of from 0.2 to 2.0 parts by weight per 100 parts of rubber by weight.

5. The composition of claim 2 wherein the rubber comprises polyisoprene or a polymer from butadiene.

6. The composition of claim 5 wherein the vulcanization accelerator is present in an amount of from 0.2 to 2.0 parts by weight per 100 parts of rubber by weight.

7. The composition of claim 2 wherein $R_1$ and $R_2$ are the same.

8. The composition of claim 7 wherein $R_1$ and $R_2$ are selected from alkyl of 3-8 carbon atoms and phenyl.

9. The composition of claim 7 wherein $R_3$ is selected from alkyl of 2-8 carbon atoms, benzyl, cyclohexyl and phenyl, optionally substituted by a chloro or carboalkoxy group.

10. The composition of claim 9 wherein the alterative is

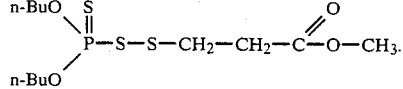

11. The composition of claim 10 wherein the accelerator is selected from azoles and sulfenamides.

12. The composition of claim 10 which contains carbon black.

* * * * *

UNITED STATES PATENT AND TRADEMARK OFFICE
CERTIFICATE OF CORRECTION

PATENT NO. : 4,496,683
DATED : January 29, 1985
INVENTOR(S) : Eiichi Morita

It is certified that error appears in the above-identified patent and that said Letters Patent are hereby corrected as shown below:

Column 4, line 28, "of" should read --on--.

Column 4, line 47, the "d" in dithiocarbamate should be capitalized since it is the beginning of the sentence.

Column 5, line 36, "1 ∝ 12" should read --1-12--.

Column 6, line 12, "alternatives" should read --alteratives--.

Column 7, line 67, "178,2g" should read --178.2g--.

Column 9, line 5, "thiophlsphoric" should read --thiophosphoric--.

Column 9, line 32, "he" should read --the--.

In Table 1, Col. 10, under DCBS, "3.7" second occurrence should read --4.7--.

Column 12, line 43, "parts" first occurrence should read --part--.

Signed and Sealed this

Ninth Day of July 1985

[SEAL]

Attest:

DONALD J. QUIGG

Attesting Officer        Acting Commissioner of Patents and Trademarks